United States Patent
Doudian et al.

(10) Patent No.: US 11,818,782 B2
(45) Date of Patent: *Nov. 14, 2023

(54) ADJUSTMENT OF ADVERTISING INTERVAL IN COMMUNICATIONS BETWEEN AN IMPLANTABLE MEDICAL DEVICE AND AN EXTERNAL DEVICE

(71) Applicant: Boston Scientific Neuromodulation Corporation, Valencia, CA (US)

(72) Inventors: Berj Doudian, Sun Valley, CA (US); Chirag Shah, Valencia, CA (US); Joshua Uyeda, Los Angeles, CA (US); Sridhar Kothandaraman, Valencia, CA (US); John Rivera, Oxnard, CA (US); Damon Moazen, Northridge, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,942

(22) Filed: Dec. 20, 2022

(65) Prior Publication Data

US 2023/0128277 A1 Apr. 27, 2023

Related U.S. Application Data

(63) Continuation of application No. 17/447,387, filed on Sep. 10, 2021, now Pat. No. 11,576,223.
(Continued)

(51) Int. Cl.
*H04W 76/10* (2018.01)
*H04W 76/30* (2018.01)
(Continued)

(52) U.S. Cl.
CPC ........ *H04W 76/15* (2018.02); *A61N 1/37223* (2013.01); *A61N 1/37252* (2013.01);
(Continued)

(58) Field of Classification Search
CPC ....... H04W 76/15; H04W 4/80; H04W 76/38; H04W 76/10; H04W 76/30;
(Continued)

(56) References Cited

U.S. PATENT DOCUMENTS 6,516,227 B1   2/2003   Meadows et al.
7,242,981 B2   7/2007   Ginggen
(Continued)

FOREIGN PATENT DOCUMENTS

WO   2021/046120   3/2021

OTHER PUBLICATIONS

Boston Scientific Corp., "Vercise™ DBS Control 4: Directions for Use" (2020; downloaded from Internet Sep. 14, 2020).
(Continued)

*Primary Examiner* — Andrew Wendell
(74) *Attorney, Agent, or Firm* — Lewis & Reese, PLLC (57) ABSTRACT

An advertising algorithm is disclosed which operates in an Implantable Medical Device (IMD) to adjust an interval at which the IMD will transmit advertising data packets to an external device able to connect with the IMD. When a communication session between the IMD and an external device is terminated, the advertising algorithm will issue advertising data packets at a higher rate for a set duration. This will allow the external device to connect more quickly with the IMD in a next communication session. After the set duration, when it may be assumed that the external device is less likely to connect with the IMD, the algorithm reduces that rate at which advertising data packets are issued, which saves power in the IMD.

20 Claims, 5 Drawing Sheets

Related U.S. Application Data (60) Provisional application No. 63/085,569, filed on Sep. 30, 2020.

(51) Int. Cl.
  *H04W 76/15* (2018.01)
  *H04W 76/38* (2018.01)
  *H04W 4/80* (2018.01)
  *A61N 1/372* (2006.01)
  *A61N 1/36* (2006.01)

(52) U.S. Cl.
  CPC .............. *H04W 4/80* (2018.02); *H04W 76/38* (2018.02); *A61N 1/36125* (2013.01)

(58) Field of Classification Search
  CPC ............ A61N 1/37223; A61N 1/37252; A61N 1/36125; A61N 1/37235; A61N 1/3727; A61N 1/37276; H04B 3/544; H04B 7/18558
  See application file for complete search history.

(56) References Cited

U.S. PATENT DOCUMENTS

| | | | |
|---|---|---|---|
| 7,672,726 | B2 | 3/2010 | Ginggen |
| 7,996,079 | B2 | 8/2011 | Armstrong |
| 8,014,867 | B2 | 9/2011 | Cooke et al. |
| 8,090,445 | B2 | 1/2012 | Ginggen |
| 8,131,377 | B2 | 3/2012 | Shi et al. |
| 8,150,516 | B2 | 4/2012 | Levine et al. |
| 8,543,207 | B2 | 9/2013 | Cooke et al. |
| 8,838,254 | B2 | 9/2014 | McClure et al. |
| 8,983,615 | B2 | 3/2015 | Tahmasian et al. |
| 9,411,027 | B2 | 8/2016 | Von Arx et al. |
| 9,446,252 | B2 | 9/2016 | Benson |
| 9,463,322 | B2 | 10/2016 | Wingeier et al. |
| 9,463,325 | B1 | 10/2016 | Young et al. |
| 9,707,402 | B2 | 7/2017 | Aghassian |
| 9,855,433 | B2 | 1/2018 | Shahandeh et al. |
| 9,867,983 | B2 | 1/2018 | Doerr |
| 9,894,691 | B1 | 2/2018 | Hellman et al. |
| 9,913,990 | B2 | 3/2018 | Ter-Petrosyan et al. |
| 10,286,209 | B2 | 5/2019 | Yoon et al. |
| 10,525,252 | B2 | 1/2020 | Feldman et al. |
| 10,589,090 | B2 | 3/2020 | Feldman et al. |
| 10,716,937 | B2 | 7/2020 | Feldman et al. |
| 11,298,552 | B2 | 4/2022 | Wu et al. |
| 11,315,683 | B2 | 4/2022 | Yoder et al. |
| 11,576,223 | B2 * | 2/2023 | Doudian ............... H04W 76/38 |
| 2007/0191914 | A1 | 8/2007 | Stessman |
| 2008/0319497 | A1 | 12/2008 | Griffith et al. |
| 2010/0272049 | A1 | 4/2010 | Tung et al. |
| 2012/0095529 | A1 | 4/2012 | Parramon et al. |
| 2015/0080982 | A1 | 3/2015 | Funderburk |
| 2015/0231402 | A1 | 8/2015 | Aghassian |
| 2015/0360038 | A1 | 12/2015 | Zottola et al. |
| 2016/0184591 | A1 | 6/2016 | Feldman et al. |
| 2017/0056677 | A1 | 3/2017 | Zhang et al. |
| 2017/0157411 | A1 | 6/2017 | Shahandeh et al. |
| 2018/0049251 | A1 | 2/2018 | Hellman et al. |
| 2018/0071513 | A1 | 3/2018 | Weiss et al. |
| 2018/0071520 | A1 | 3/2018 | Weerakoon et al. |
| 2018/0140831 | A1 | 5/2018 | Feldman et al. |
| 2018/0152972 | A1 | 5/2018 | Wu et al. |
| 2018/0243568 | A1 | 8/2018 | Demmer et al. |
| 2019/0344087 | A1 | 11/2019 | Ter-Petrosyan et al. |
| 2019/0381326 | A1 | 12/2019 | Shahandeh et al. |
| 2020/0001091 | A1 | 1/2020 | Marnfeldt |
| 2020/0129773 | A1 | 4/2020 | Eisele et al. |
| 2020/0260320 | A1 | 8/2020 | Ramanathan et al. |
| 2021/0167872 | A1 | 6/2021 | Nagata |

OTHER PUBLICATIONS

Boston Scientific Corp., "Vercise™ Neural Navigator 4 Programming Manual: Directions for Use" (2020; downloaded from Internet Sep. 14, 2020).

Boston Scientific Corp., "ImageReady™ MRI Guidelines for Boston Scientifc Deep Brain Stimulation Systems" (2020; downloaded from Internet Sep. 14, 2020).

Boston Scientific Corp., Vercise™ DBS Remote Control 4 Handbook (2020).

Cypress Semiconductor Corp., "PSoC Creator Component Datasheet: Bluetooth Low Energy (BLE) 1.20," p. 34 (2015).

Recommendation ITU-R RS 1346: Sharing Between the Meteorlogical Aids Service and Medical Implant Communication Systems (MICS) Operating in the Mobile Service in the Frequency Band 401-406 MHZ (1998).

Texas Instruments Inc., data sheet for "CC2640R2F SimpleLink™ Bluetooth® 5.1 Low Energy Wireless MCU" (Jan. 2020).

International Search Report and Written Opinion regarding corresponding PCT Application No. PCT/US2021/071428, dated Jan. 5, 2022.

* cited by examiner

ADJUSTMENT OF ADVERTISING INTERVAL IN COMMUNICATIONS BETWEEN AN IMPLANTABLE MEDICAL DEVICE AND AN EXTERNAL DEVICE

CROSS REFERENCE TO RELATED APPLICATIONS

This is a continuation of U.S. patent application Ser. No. 17/447,387, filed Sep. 10, 2021, which is a non-provisional of U.S. Provisional Patent Application Ser. No. 63/085,569, filed Sep. 30, 2020. These applications are incorporated herein by reference, and priority is claimed to them.

FIELD OF THE INVENTION

This application deals with implantable medical device (IMDs) systems and manners in which external devices can communicate with an IMD.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) or Spinal Cord Stimulation (SCS) system, such as that disclosed in U.S. Pat. No. 6,516,227 and U.S. Patent Application Publication 2016/0184591. However, the present invention may find applicability with any implantable neurostimulator device system, including peripheral nerve stimulation systems.

Figure 1:
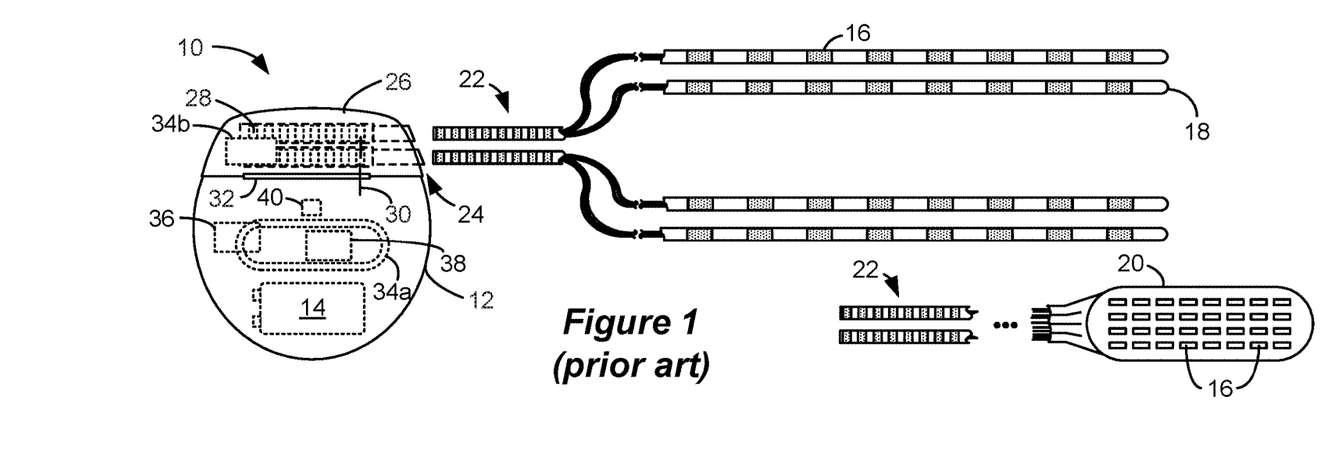
FIG. 1 shows an Implantable Pulse Generator (IPG), in accordance with the prior art.

A DBS or SCS system typically includes an Implantable Pulse Generator (IPG) 10 shown in FIG. 1. The IPG 10 includes a biocompatible device case 12 that holds the circuitry and a battery 14 for providing power for the IPG to function. Battery 14 may comprise a rechargeable battery or a primary cell battery which is not rechargeable. The IPG 10 is coupled to tissue-stimulating electrodes 16 via one or more electrode leads that form an electrode array. For example, one or more percutaneous leads 18 can be used having electrodes 16 carried on a flexible body. In another example, a paddle lead 20 provides electrodes 16 positioned on one of its generally flat surfaces. Lead wires within the leads are coupled to the electrodes 16 and to proximal contacts 22 insertable into lead connectors 24 fixed in a header 26 on the IPG 10, which header can comprise an epoxy for example. Once inserted, the proximal contacts 22 connect to header contacts 28 within the lead connectors 24, which are in turn coupled by feedthrough pins 30 through a case feedthrough 32 to stimulation circuitry 36 within the case 12. The number and type of leads, and the number of electrodes on such leads, can vary depending on the application. The conductive case 12 can also comprise an electrode.

In a SCS application, as is useful to alleviate chronic back pain for example, the electrode lead(s) are typically implanted in the spinal column proximate to the dura in a patient's spinal cord, preferably spanning left and right of the patient's spinal column. The proximal contacts 22 are tunneled through the patient's tissue to a distant location such as the buttocks where the IPG case 12 is implanted, at which point they are coupled to the lead connectors 24. In a DBS application, as is useful in the treatment of tremor in Parkinson's disease for example, the IPG 10 is typically implanted under the patient's clavicle (collarbone). Percutaneous leads 18 are tunneled through and under the neck and the scalp where the electrodes 16 are implanted through holes drilled in the skull and positioned for example in the subthalamic nucleus (STN) and the pedunculopontine nucleus (PPN) in each brain hemisphere.

IPG 10 can also comprise functionally-similar devices that are not fully implantable in the patient, such as an External Trial Stimulator (ETS). An ETS has leads implantable in the patient but connected to a circuitry portion that is external to the patient. When an ETS is used, stimulation can be tried on a prospective implant patient without going so far as to implant the IPG's case 12. ETS devices are explained further in U.S. Published Patent Application 2020/0001091. For purpose of this disclosure, an IPG should be understood to include ETSs as well.

IPG 10 can include an antenna 34a allowing it to communicate bi-directionally with a number of external devices discussed subsequently. Antenna 34a as shown comprises a conductive coil within the case 12, although the coil antenna 34a can also appear in the header 26. When antenna 34a is configured as a coil, communication with external devices preferably occurs using near-field magnetic induction, using a communication scheme like Frequency Shift Keying (FSK) for example. See, e.g., U.S. Patent Application Publication 2015/0080982 (describing the use of FSK in magnetic-inductive implantable medical device telemetry). IPG 10 may also include a Radio-Frequency (RF) antenna 34b. In FIG. 1, RF antenna 34b is shown within the header 26, but it may also be within the case 12. RF antenna 34b may comprise a patch, slot, or wire, and may operate as a monopole or dipole. RF antenna 34b preferably communicates using far-field electromagnetic waves, and may operate in accordance with any number of known RF communication standards, such as Bluetooth, Bluetooth Low Energy (BLE), Zigbee, WiFi, MICS, and the like.

Stimulation in IPG 10 is typically provided by pulses, as described in the above-referenced '091 Publication. Pulses can be formed by stimulation circuitry 36 in the IPG, again as described in the '091 Publication. Stimulation circuitry 36 can comprise a part of, or can communicate with, the IPG's control circuitry 38. The control circuitry 38 can comprise a microcontroller, microprocessor, Field Programmable Grid Array, Programmable Logic Device, Digital Signal Processor or like devices. In one example, control circuitry 38 can comprise or include an MSP430 microcontroller device, manufactured by Texas Instruments, Inc. Control circuitry 38 may also be based on well-known ARM microcontroller technology. Control circuitry 38 may include a central processing unit capable of executing instructions, with such instructions stored in volatile or non-volatile memory within the control circuitry. Control circuitry 38 may also include, operate in conjunction with, or be embedded within, an Application Specific Integrated Circuit (ASIC), such as described in U.S. Patent Application Publications 2008/0319497, 2012/0095529, 2018/0071513, or 2018/0071520, which are incorporated herein by reference. The control circuitry 38 may comprise an integrated circuit with a monocrystalline substrate, or may comprise any number of such integrated circuits. Control circuitry 38 may also be included as part of a System-on-Chip (SoC) or a System-on-Module (SoM) which may incorporate memory devices and other digital interfaces.

IPG 10 may also include a magnetic field sensor 40, such as a Hall effect sensor. Magnetic field sensor 40 can also comprise other devices or circuits in the IPG, for example as taught in U.S. Pat. No. 10,589,090 and U.S. Patent Application Publication 2007/0191914. Use of the magnetic field sensor 40 in an IPG 10 is explained further below.

Figure 2:
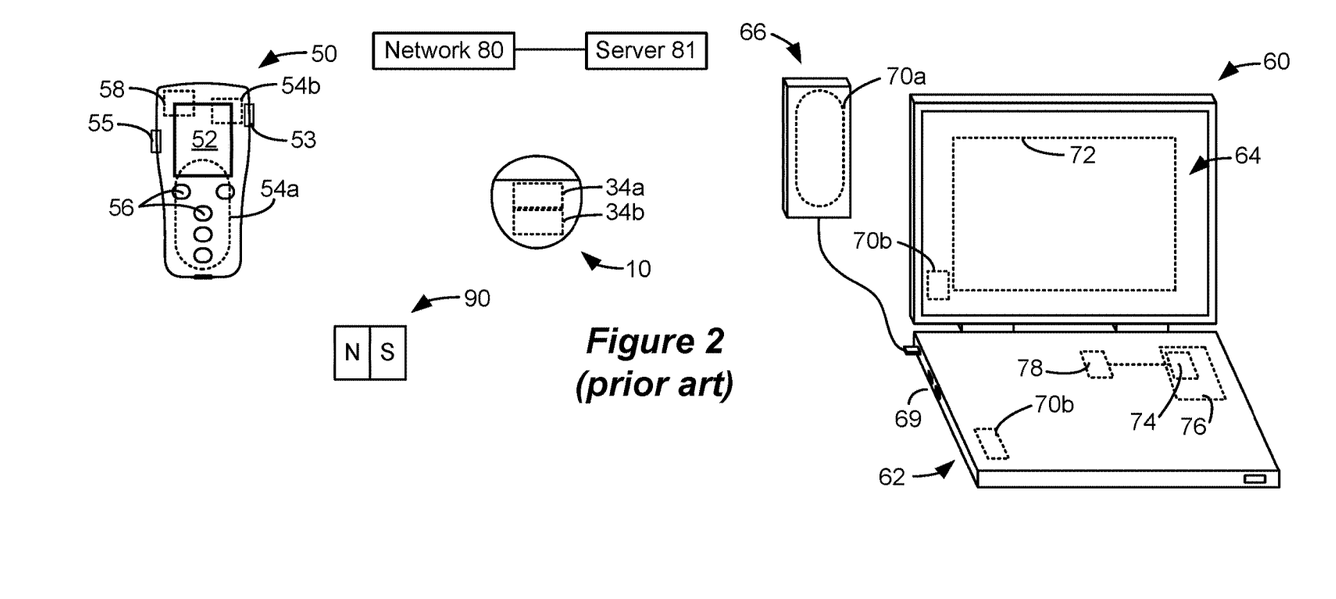
FIG. 2 shows various external devices capable of communicating with and programming stimulation in an IPG, in accordance with the prior art.

FIG. 2 shows various external devices that can wirelessly communicate with the IPG 10, including a patient hand-held remote controller (RC) 50 and a clinician programmer (CP) 60. Both of devices 50 and 60 can be used to wirelessly transmit information, such as a stimulation program, to the IPG 10—that is, to program stimulation circuitry 36 to produce stimulation (e.g., pulses) with a desired amplitude and timing. Both devices 50 and 60 may also be used to adjust one or more stimulation parameters of a stimulation program that the IPG 10 is currently executing, to update software in these devices, or to place the IPG into different operational modes as discussed further below. Devices 50 and 60 may also wirelessly receive information from the IPG 10, such as various status information, etc.

Clinician programmer (CP) 60 is described further in U.S. Patent Application Publication 2015/0360038, and can comprise a computing device 62, such as a desktop, laptop, notebook computer, tablet, mobile smart phone, or Personal Data Assistant (PDA)-type mobile computing device, etc. In FIG. 2, computing device 62 is shown as a laptop computer that includes typical computer user interface means such as a screen 64, a mouse, a keyboard, speakers, a stylus, a printer, etc., not all of which are shown for convenience. Also shown in FIG. 2 are accessory devices for the CP 60 that are usually specific to its operation as a stimulation controller, such as a communication "wand" 66 coupleable to suitable ports (e.g., USB ports 69) on the computing device 62.

The antenna used in the CP 60 to communicate with the IPG 10 can depend on the type of antennas included in the IPG. If the patient's IPG 10 includes a coil antenna 34a, wand 66 can likewise include a coil antenna 70a to establish near-field magnetic-induction communications at small distances. In this instance, the wand 66 may be affixed in close proximity to the patient, such as by placing the wand in a belt or holster wearable by the patient and proximate to the patient's IPG 10. If the IPG 10 includes an RF antenna 34b, the wand 66, the computing device 62, or both, can likewise include an RF antenna 70b to establish communication at larger distances.

To program stimulation programs or parameters for the IPG 10, or to otherwise control the IPG 10, the clinician interfaces with a clinician programmer graphical user interface (GUI) 72 provided on the display 64 of the computing device 72. As one skilled in the art understands, the GUI 72 can be rendered by execution of clinician programmer software 74 stored in the computing device 72, which software may be stored in the device's non-volatile memory 76. Execution of the clinician programmer software 74 in the computing device 62 can be facilitated by control circuitry 78 such as one or more microprocessors, microcomputers, FPGAs, DSPs, other digital logic structures, etc., which are capable of executing programs in a computing device, and which may comprise their own memories. For example, control circuitry 78 can comprise an i5 processor manufactured by Intel Corp, as described at https://www.intel.com/content/www/us/en/products/processors/core/i5-processors.html. Such control circuitry 78, in addition to executing the clinician programmer software 74 and rendering the GUI 72, can also enable communications via antennas 70a or 70b to communicate stimulation parameters chosen through the GUI 72 to the patient's IPG 10.

Remote controller (RC) 50 can be as described in U.S. Patent Application Publication 2015/0080982 for example, and may comprise a controller dedicated to work with the IPG 10. RC 50 may also comprise a general purpose mobile electronics device such as a mobile phone which has been programmed with a Medical Device Application (MDA) allowing it to work as a wireless controller for the IPG 10, as described in U.S. Patent Application Publication 2015/0231402. Like the CP 60, RC 50 includes a graphical user interface including a display 52 and means for entering commands or selections, such as buttons 56 or selectable graphical elements rendered on the display. The RC 50's graphical user interface also enables a patient to adjust stimulation parameters, although it may have limited functionality when compared to the more-powerful CP 60 described above. The RC 50 may also include a lock screen button 53 to unlock the display and otherwise power up the RC after it has gone into a power-down mode, and a programming button 55 as explained further below.

The RC 50 can have one or more antennas capable of communicating with the IPG 10. For example, the RC 50 can have a near-field magnetic-induction coil antenna 54a capable of wirelessly communicating with the coil antenna 34a in the IPG 10. The RC 50 can also have a far-field RF antenna 54b capable of wirelessly communicating with the RF antenna 34b in the IPG 10. The RC 50 includes control circuitry 58 which may be similar to the control circuitry in the CP 60, and which includes memory for storing software and the like. The RC 50 typically has a battery (not shown) to provide operating power, and such battery is usually rechargeable (similar to a cell phone).

The IPG 10, RC 50, and CP 60, as well as communicating with each other, can communicate with a network 80. Network 80 can comprise a WiFi gateway and the Internet for example, and communication between the devices can occur using the network 80 as an intermediary. A server 81 can be connected to the network, which can for example be used to send stimulation programs or other useful information (e.g., software updates) to the various devices in the system.

FIG. 2 further shows a permanent bar magnet 90 in the communication system for the IPG 10. Use and function of the bar magnet 90 is described further below.

SUMMARY

An implantable medical device (IMD) is disclosed that is configured to communicate with an external device. The IMD may comprise: control circuitry programmed with an advertising algorithm, wherein the advertising algorithm is configured to: establish a first communication session with the external device, wherein the first communications session enables the exchange of first data between the external device and the IMD; terminate the first communication session; and upon terminating the first communication session, cause advertisement data to be repeatedly transmitted to the external device, wherein the advertisement data is configured to allow the external device to establish a second communication session with the IMD; increase a time interval between the transmitted advertisement data packets over time.

In one example, the control circuitry is programmed with an inactivity duration, wherein the advertising algorithm is configured to terminate the first communication session after the inactivity duration is exceeded. In one example, the advertising algorithm is configured to determine a first time when the first data is no longer being exchanged during the first communication session, wherein the advertising algorithm is configured to terminate the first communication session when a duration after the first time exceeds the inactivity duration. In one example, the advertising algorithm is configured to terminate the first communication session by transmitting a disconnection instruction to the external device. In one example, the advertising algorithm is configured to establish the first communication session by receiving a connection request from the external device. In one example, the advertising algorithm is further configured to establish the first communication session by transmitting an acknowledgment to the external device in response to the connection request. In one example, the advertising algorithm is configured, upon terminating the first communication session, to cause the advertisement data to be repeatedly transmitted to the external device at a first time interval for a first duration, and thereafter to cause the advertisement data to be repeatedly transmitted to the external device at a second time interval, wherein the first time interval is shorter than the second time interval. In one example, the control circuitry is configured to store programmable values for the first duration, the first time interval, and the second time interval. In one example, the advertising data comprises an identification code for the IMD. In one example, the advertising data is transmitted using a Bluetooth or Bluetooth Low Energy communication standard. In one example, the advertising algorithm is further configured to establish the second communication session with the external device, wherein the second communications session enables the exchange of second data between the external device and the IMD. In one example, the control circuitry stores pairing information for the external device indicating that the IMD and external device are paired, wherein the advertising algorithm is configured to establish the first communication session with the paired external device.

A method is disclosed for facilitating communications between an implantable medical device (IMD) and an external device. The method may comprise: establishing a first communication session between the external device and the IMD, wherein the first communications session enables the exchange of first data between the external device and the IMD; terminating the first communication session; and upon terminating the first communication session, repeatedly transmitting from the IMD advertisement data to the external device, wherein the advertisement data is configured to allow the external device to establish a second communication session with the IMD, wherein a time interval between the transmitted advertisement data packets increases over time.

In one example, the first communication session is terminated after an inactivity duration stored in the IMD is exceeded. In one example, the method further comprises determining a first time when the first data is no longer being exchanged during the first communication session, wherein the first communication session is terminated a duration after the first time exceeds the inactivity duration. In one example, the first communication session is terminated by transmitting a disconnection instruction from the IMD to the external device. In one example, the first communication session is established by receiving at the IMD a connection request from the external device. In one example, the first communication session is established by transmitting an acknowledgment from the IMD to the external device in response to the connection request. In one example, upon terminating the first communication session, the advertisement data is repeatedly transmitted to the external device at a first time interval for a first duration, and thereafter the advertisement data is repeatedly transmitted to the external device at a second time interval, wherein the first time interval is shorter than the second time interval. In one example, the method further comprises programming into the IMD values for the first duration, the first time interval, and the second time interval. In one example, the advertising data comprises an identification code for the IMD. In one example, the advertising data is transmitted using a Bluetooth or Bluetooth Low Energy communication standard. In one example, the method further comprises establishing the second communication session between the external device and the IMD, wherein the second communications session enables the exchange of second data between the external device and the IMD. In one example, the method further comprises pairing the external device with the IMD, wherein the first communication session is established between the paired external device and the IMD.

DETAILED DESCRIPTION

As noted earlier, communications between an IPG 10 and an external device such as the remote controller (RC) 50 or clinician programmer (CP) 60 can occur in accordance with a communication scheme such as Bluetooth or Bluetooth Low Energy (BLE). BLE is favored as a standard for such communications as it includes mechanisms that reduce power consumption in the devices. This is especially beneficial as concerns the IPG 10. As noted earlier, the IPG 10 includes a battery 14 to provide its power, and it is preferred that communications not unduly drain this battery. If communication schemes are used that are too power intensive, the IPG 10 will need to be replaced early if the battery 14 is a primary cell, or recharged too frequently if the battery is rechargeable.

When a communication standard such as BLE is used between the IPG 10 and an external device, the devices will operate in either a central role or a peripheral role, with the BLE chips in the devices being programmed to operate in these roles. Typically, the IPG 10 acts in the peripheral role, and so is able advertise its presence (provide advertising data packets) to allow an external device to which it is paired to connect with the IPG 10. The external device, acting in the central role, is able to scan for the IPG 10 and to receive its advertising data, which then allows the external device to connect to the IPG 10. After a central role device and peripheral role device connect, a communication session is started, with these devices respectively operating as a server (master) and client (slave) to transmit data between them as dictated by the BLE standard.

A goal of BLE communications, as already noted, is to reduce power consumption, and in this regard advertising data is broadcast only periodically from the IPG 10. This means that the IPG 10 need only enable and power its telemetry circuitry (e.g., antenna 34*b* and its related modulation/demodulation circuitry) for limited times. The constant time interval at which advertising data packets are broadcast is programmable, and typically is programmed into the BLE chip that governs the IPG's communications. This advertising interval can range from 20 ms to as long as 10.24 seconds. In reality, advertising data is transmitted on up to three dedicated channels (frequencies) to reduce interference. Still further, to avoid consecutive collisions, a random delay of up to 10 ms can be added to each advertising data packet. That being said, the advertising interval is still said to be constant for all intents and purposes.

The constant advertising interval can thus be adjusted (increased) to reduce power consumption in the IPG 10. However, in the inventors' view, this can come at a disadvantage. The goal of the IPG 10 in advertising its presence is to enable a paired external device to connect with it so that a communication session can be established between them, during which data can be exchanged. For example, during such a communication session, a user (patient or clinician) can use their RC 50 or CP 60 to transmit new stimulation parameters for the IPG 10 to execute. Eventually, the established communication session will end. As explained further below, this can occur automatically when the IPG 10 and the external device stop transmitting data. Specifically, the IPG can end the communication session after data transmission between the IPG 10 and external device have ceased for an inactivity duration. Because maintaining the communication session takes power in the IPG 10, this inactivity period is preferably kept to a minimum (e.g., a few minutes) so as not to waste power in the IPG 10. Once the communication session has ended, the IPG 10 will again begin transmitting its advertisement data at its constant advertising interval. That way, the external device can again connect with the IPG if need be, and a second communication session can be established.

But this can be frustrating from the perspective of the user of the external device. Suppose for example that a clinician is using an external device such as CP 60 to try and find optional stimulation parameters for a patient. This may occur during a patient fitting session, which may take tens of minutes, or even hours. At a first point in time, the clinician may use the CP 60 to transmit stimulation parameters to the patient's IPG 10 during a first communication session. It may then be a while (several minutes) before the clinician uses the CP 60 again to transmit new stimulation parameters, at which time the first communication session may have ended and the IPG 10 and external device are disconnected. The CP 60 can connect again to the IPG 10, but it will have to wait until it receives an advertising data packet to do so. If the constant advertising interval is set to a long value (to save power in the IPG 10), it may be slow to establish this connection. This is particularly true if an advertising data packet is not reliably received at the external device and thus the external device needs to wait for receipt of a next advertising packet. As a result, the clinician may not be able to transmit the new stimulation parameters quickly to the IPG 10. Particularly if the fitting session with the patient is long, with the external device and IPG 10 needing to connect and disconnect several times, delay in reestablishing communication sessions with the IPG can negatively impact the timeliness of the programming session. This problem is exacerbated if the inactivity duration is set to a short value in the IPG 10 (again, to save power), as this will cause the IPG to disconnect from communication sessions more quickly.

To address this concern, the inventors disclose an advertising algorithm, which can operate in the IPG 10 to adjust the interval at which the IPG will transmit advertising data packets. When a communication session between the IPG and an external device is terminated, the advertising algorithm will issue advertising data packets at a higher rate for a set duration. This will allow the external device to connect more quickly with the IPG. After the set duration, when it may be assumed that the external device is less likely to connect with the IPG, the algorithm reduces the rate at which advertising data packets are issued, which saves power in the IPG.

Figure 3:
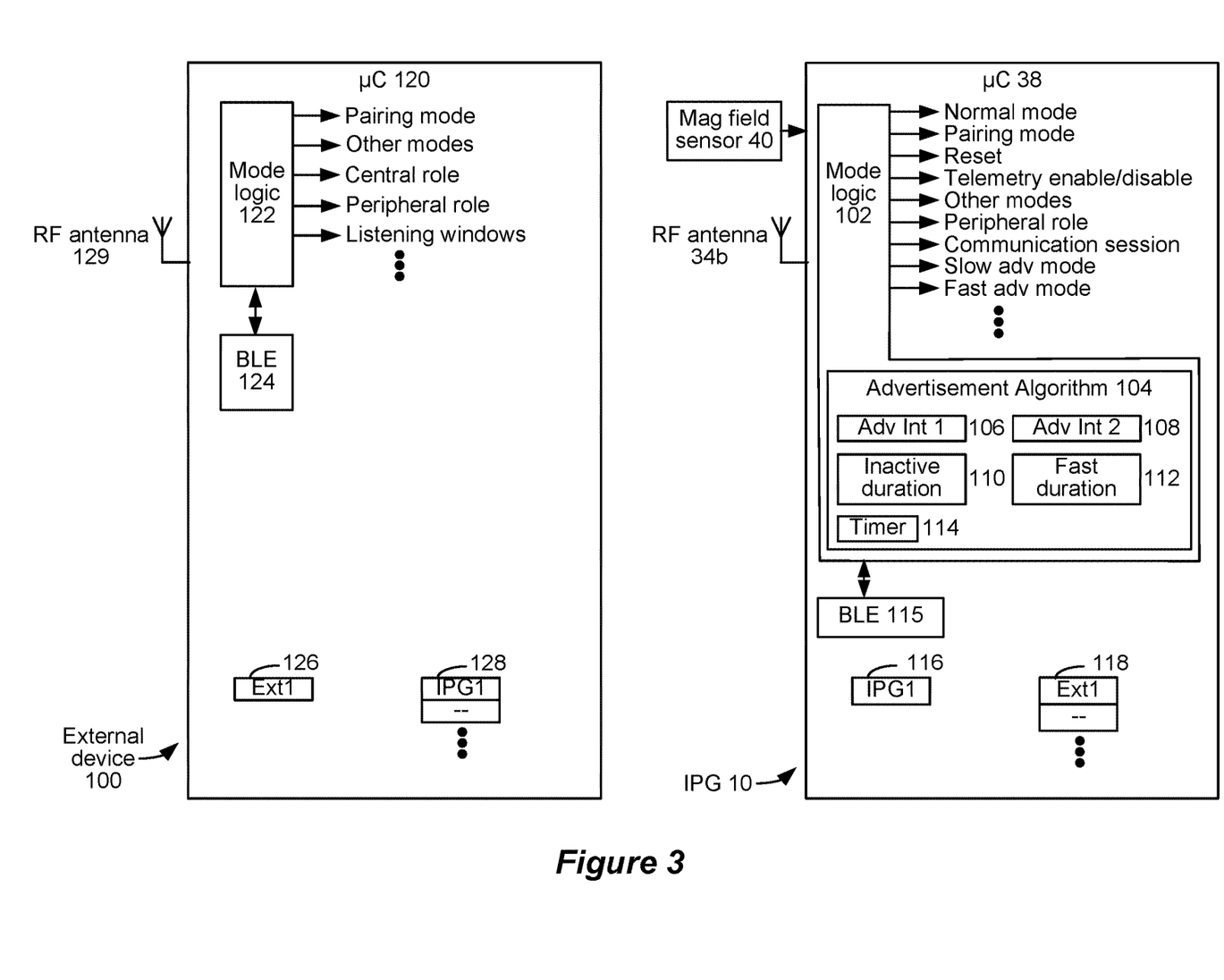
FIG. 3 shows further details of an IPG containing an advertisement algorithm, and an external device such as a remote controller (RC) or a clinician programmer (CP).

FIG. 3 shows circuitry that is implicated by the disclosed technique in the IPG 10 and an external device 100. External device 100 can represent either the remote controller (RC) 50 or the clinician programmer (CP) 60 described earlier, or another external device capable of communicating with the IPG 10. In this example, it is assumed that communications between the IPG 10 and the external device 100 are RF in nature, and preferably occur using the BLE communication standard. As such, the IPG 10 and external device 100 have RF antennas 34*b* and 129, with RF antenna 129 comprising antenna 54*b* in the RC 50 or antenna 70*b* in the CP 60. Communications could also occur using magnetic induction (e.g., FSK), in which case the antennas would comprise coil antennas, as described previously.

The IPG 10's control circuitry 38 is programmed with mode logic 102 which can set the IPG 10 into different modes, and can issue control signals consistent with those modes. For example, the IPG 10 can operate in a normal mode, which comprises the basic mode in which the IPG is active and providing stimulation to the patient, and where telemetry is enabled with a paired external device. Mode logic 102 can also cause IPG 10 to operate in a pairing mode to allow the IPG to be paired for communications with the external devices 100. Pairing can occur using a bar magnet 90 (FIG. 2). Briefly, the bar magnet 90 can be held proximate to the IPG's magnetic field sensor 40, which can inform the mode logic 102 in IPG 10 to enter the pairing mode. The details of how the IPG 10 and external device 100 can be paired, and the information exchanged when doing so, is unnecessary to elaborate upon here. Use of the bar magnet 90 can also be used to reset the IPG 10, which causes stimulation to cease.

Mode logic 102 can also cause the IPG 10 to operate in a peripheral role, which as noted above enables the IPG 10 advertise its presence (provide advertising data packets) to external devices to which it is paired. Mode logic 102 can further cause the IPG 10 to enter into a communication session with an external device, and to enter either a slow or fast advertising mode, as explained further below. Control of the peripheral role, communication sessions, and operation in the slow or fast advertising modes can occur through use of an advertisement algorithm 104 explained further below. Mode logic 102 can also cause the IPG to operate in other modes not of importance here.

As just noted, the IPG 10 can include an advertisement algorithm 104, which may be programmed into the IPG 10's control circuitry 38, and more specifically may comprise part of the IPG's mode logic 102. The advertising algorithm 104 generally speaking dictates how the IPG 10 will advertise its presence, and under what circumstances, as explained further below. Aspects of the advertising algorithm 104 are preferably programmable, and the algorithm 104 may include or communicate with a number of programmable memories that hold parameters of interest.

For example, memory 106 can store a value for a first advertising interval (Adv Int 1) which dictates a first set time interval at which the IPG 10 will issue advertising data packets. In the example that follows, this first advertising interval is a longer interval that operates during the slow advertising mode. In one example, the first advertising interval may be approximately 2.9 seconds. Memory 108 can store a value for a second advertising interval (Adv Int 2) which dictates a second set time interval at which the IPG 10 will issue advertising data packets. In the example that follows, this second advertising interval is a shorter interval that operates during the fast advertising mode. In one example, the second advertising interval may be on the order of tenths of seconds, such as 0.3 seconds.

Memory 110 sets a value for an inactivity duration. The inactivity duration comprises a time period of inactivity during a communication session. When this time period is exceeded, the advertisement algorithm 104 causes the IPG 10 to enter the fast advertising mode, as explained further below. In one example, the inactivity duration may be on the order of one minute or so. Memory 112 sets a value for the duration of the fast advertising mode, and after the expiration of this duration the advertising algorithm 104 causes the IPG 10 to enter the slow advertising mode. In one example, the inactivity duration may be on the order of one minute or so. The fast advertising mode duration may be on the order of a few minutes, such as 3 minutes. A timer 114 can be used to control and monitoring the various timings that are used in the advertising algorithm 104. The values in memories 106-112 can be programmed or adjusted using the GUI of the external device 100, although the interface for doing so isn't shown for simplicity.

The advertising algorithm 104 preferably works in conjunction with a communications chip, such as BLE chip 115. BLE chip 115 as per its normal function can control many of the communication aspects in the IPG 10, and is preferably programmable by the advertising algorithm 104. For example, when the advertising algorithm 104 decides to enter the slow or fast advertising modes, the algorithm 104 can transmit the relevant advertising intervals (Adv Int 1 of Adv Int 2) to the BLE chip 115 for implementation. In this regard, the BLE chip 115 can include memories to hold relevant values, and may include memories duplicative of the memories 106-112, although this detail isn't shown. Alternatively, memories 106-112 can appear exclusively within the BLE chip 115. Because the BLE chip 115 can be used to control the IPG's various modes, it can be considered as part of the mode logic 102.

As also shown in FIG. 3, the external device 100 also includes control circuitry 120, which may comprise control circuitries 58 or 78 in the RC 50 or CP 60. Control circuitry 120 may also be programmed with mode logic 122 to cause the external device 100 to operate in a number of different modes. For example, the mode logic 122 can control operation in the central role, thus allowing communications to be established with the IPG 10 when it operates in the peripheral role. In other examples, the external device can operate in a peripheral role at certain times (e.g., when it needs to communicate with another external device). Mode logic 122 can also cause the external device 100 to operate in a pairing mode to allow it to be paired to the IPG 10, although as noted above such details are not relevant here. Lastly, the mode logic 122 can cause the external device to issue listening windows as is necessary for the detection of advertising data packets that may be provided by the IPG 10. As was the case in the IPG 10, the mode logic 122 can control or include a BLE chip 124.

The control circuitries 38 and 120 in the IPG 10 and external device 100 can further include memories that are relevant to establishing communications with each other. Memories 116 and 126 store the devices' ID codes (IPG1, Ext1), and possibly other credentials or certificates that allow the device to communicate with other devices in the system. These ID codes can include or comprise serial numbers for the respective devices. Memories 118 and 128 store the ID codes (and other credentials and certificates) for devices which with they have previously been paired for communications. For example, it is assumed in FIG. 3 that the external device 100 has paired with the IPG 10 and thus stores the ID code for this device (IPG1) in memory 128. Consistent with this, IPG 10 stores the ID code for the external device (Ext1) in its memory 118. Memories 118 and 128 can store the ID codes for several devices.

Figure 4A:
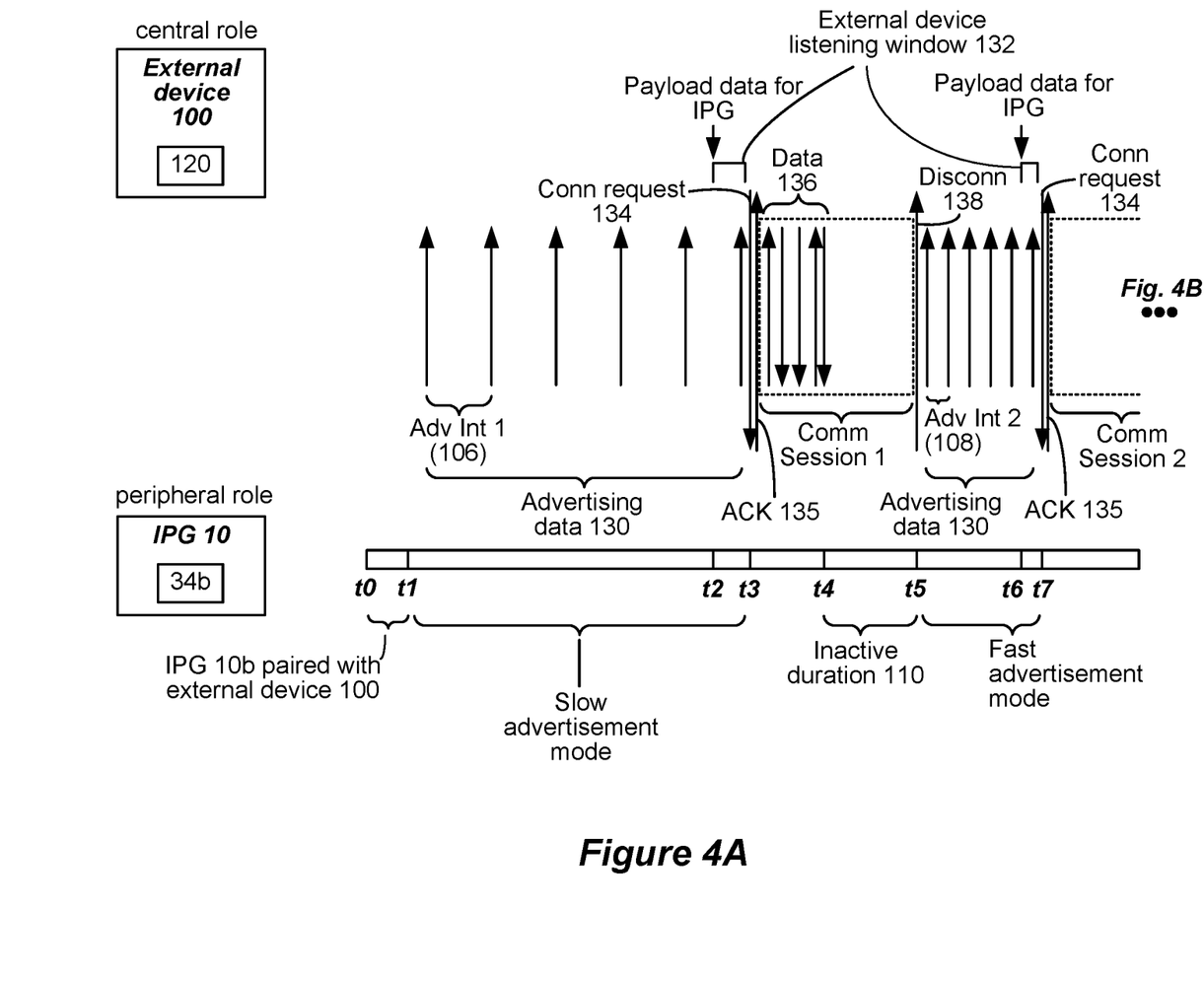
FIGS. 4A and 4B shows operation of the advertisement algorithm, and explains the data that is communicated between the IPG and the external device.
Figure 4B:
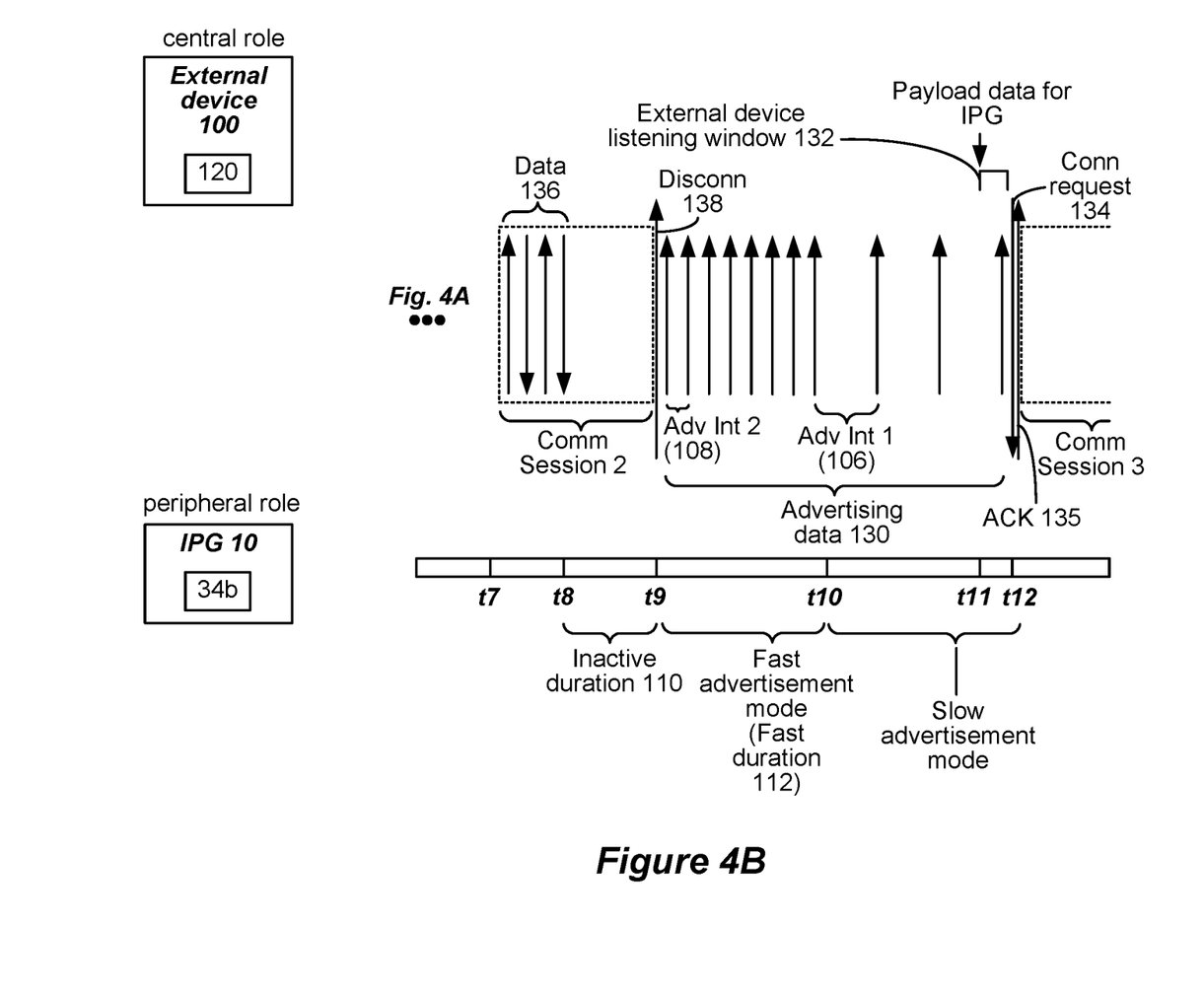
Figure 5:
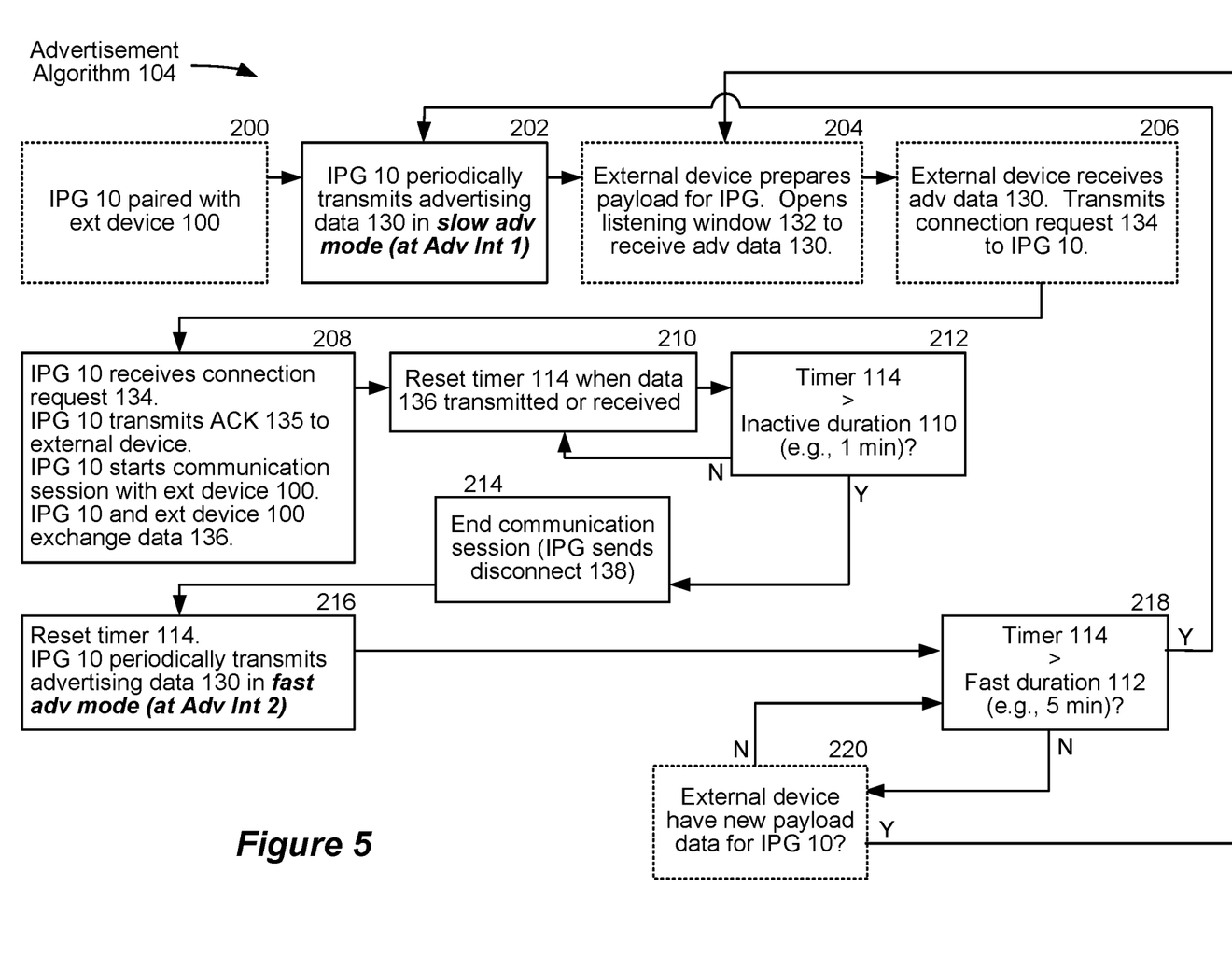
FIG. 5 is a flow chart explaining operation of the advertisement algorithm.

FIGS. 4A and 4B illustrate operation of an example of the advertising algorithm 104, and of the data that is shared between the IPG 10 and the external device 100 when this algorithm in operating. FIG. 5 describes the advertising algorithm 104 in a flow chart form, with steps performed in the IPG 10 in solid boxes, and other steps (e.g., performed by the external device) in dotted lined boxes.

Operation is explained chronologically starting with FIG. 4A, and between t0 and t1 it is assumed that the IPG 10 and external device 100 are paired (FIG. 5, 200). This step isn't necessarily part of the advertising algorithm 104, but is shown for completeness. As noted above, the IPG 10 and external device 100 can be paired in different manners (such as through use of an external bar magnet 90). Pairing will cause each of the devices to store information about the other device (its ID code, etc.), in memories 118 and 128 (FIG. 3), which facilitates their ability to form a communication session, as explained below.

At time t1, after the devices are paired, the IPG 10 preferably enters a slow advertisement mode, and begins transmitting advertising data packets 130 in accordance with the slower advertising interval (Adv Int 1; e.g., 2.9 s) stored in memory 106 (FIG. 3) (FIG. 5, 202). The slow advertisement mode can be understood as the default advertisement mode that the advertising algorithm 104 will use when the devices have not established a communication session, or when it has been some time since the last communication session, as explained further below.

At time t2, it is assumed that the external device 100 has prepared "payload data" for the IPG 10 (204, FIG. 5). This payload data can comprise different types of information, and may be sent by the external device 100 automatically or under control of the user. For example, the payload data can comprise new or adjusted stimulation parameters for the IPG 10 to execute. These stimulation parameters may have been entered into the external device 100's GUI by the user, or may be determined automatically by the external device 100. The payload data could also comprise information that doesn't involve the particulars of stimulation therapy. For example, the payroll data could comprise software updates for the IPG 10, instructions to place the IPG into a particular mode, instructions to have the IPG 10 report certain data it might have stored, etc.

In any event, once such payload data is prepared for transmission to the IPG 10, the external device 100 will issue one or more listening windows 132 (204, FIG. 5). The listening window 132 may issue automatically once the payload data is prepared. Alternatively, because the listening windows may be scheduled at the external device 100, the listening window 132 may comprise a next-scheduled listening window. During the listening window 132, the external device 100 will power its telemetry antenna 129 and any related telemetry circuitry, and await the receipt of an advertising data packet 130 being transmitted by the IPG 10. Because the IPG is currently transmitting in the slow advertising mode, the listening window 132 is preferably maintained for a duration that at least equals the first advertising interval (t1). If this interval is set to 2.9 seconds for example, the listening window 132 may need to be issued for at least this long to ensure that an advertising data packet 130 will be received. If there is interference or other factors at play that would affect the reliability of receipt of the advertising data packets 130, the listening window 132 may issue for longer until a packet 130 is reliably received. Although not shown, listening windows 132 may also issue with some periodicity (e.g., on a schedule as noted above) to save power in the external device 100. If scheduled, listening windows 132 may issue at a higher frequency when payload data for the IPG is ready at the external device 100.

Upon receipt of an advertising data packet 130, which includes the IPG 10's ID code (IPG1), the external device 100 can realize that the received packet is from a device with which it is paired (see memory 128, FIG. 3). In response, the external device 100 can stop the listening window 132, and transmit a connection request 134 to the IPG 10 at time t3 (206, FIG. 5). Upon receipt of the connection request 134, the IPG 10 can issue a connection request acknowledgment (ACK) 135 very soon thereafter. This starts a communication session (Comm Session 1) between the IPG 10 and the external device 100 shortly after time t3 (208, FIG. 5).

During the communication session, the external device 100 and IPG 10 can exchange data 136 (208, FIG. 5). Data 136 would likely include the payload data referred to earlier. The IPG 10 may also have data 136 to transmit to the external device during the communication session, either in response to the payload data, or independent of such data. For example, during a communication session, the IPG 10 may upload certain data (e.g., status data) that it has saved to the external device 100. The exchange of data 136 is governed by connection packets which can issue relatively quickly, on the order of tens of milliseconds. The telemetry antennas and communication circuitry in both the IPG 10 and the external device 100 can be constantly powered during the communication session in preparation to send or receive data packets 136. The exchange of data 136 between the external device 100 and the IPG 10 can comprise data entirely transmitted from the external device 100 to the IPG 10, data transmitted entirely from the IPG 10 to the external device 100, or data transmitted in both of these directions.

Timer 114 monitors data 136 exchange between the external device 100 and the IPG 10, and in particular monitors a duration after data exchange has ceased. This can occur in different manners, but in a simple example the timer 114 counts, but is reset when data 136 is transmitted or received during the communication session (210, FIG. 5). At time t4, it is assumed that no further data 136 is being exchanged between the external device 100 and the IPG 10, and thus the timer 114 begins counting without being reset. The advertising algorithm 104 will monitor the count of the timer 114, and when this count exceeds the programmed inactivity duration 110 (e.g., one minute) (212, FIG. 5), the algorithm 140 will end the communication session by transmitting a disconnection instruction 138, as shown at time t5 (214, FIG. 5). As noted earlier, it can be beneficial to program the inactivity duration 110 to a lower value to reduce power consumption in the IPG 10, and so that communication sessions are not needlessly extended when no data 136 is being transmitted.

Once the communication session has ended, the IPG 10 will once again start transmitting advertising data packets 130, although under control of the advertisement algorithm 140 it will so do at a faster rate in accordance with its fast advertisement mode. Specifically, the IPG 10 will begin transmitting advertising data packets 130 at the faster advertising interval (Adv Int 2, e.g., 0.3 s) stored in memory 108 (FIG. 3) (FIG. 5, 216). Preferably, advertising data packets 130 are transmitted during the fast advertisement mode for a limited fast advertising mode duration stored in memory 112 (e.g., 3 minutes) before switching to the slow advertisement mode, as explained further below. Timer 114 can be reset at the beginning of the fast advertising mode (FIG. 5, 216), with its count used to determine when the fast advertisement mode duration 112 has been exceeded (FIG. 5, 218).

Although issuing fast advertising data packets will increase power consumption in the IPG 10, it can also assist the external device 100 to re-establish a connection to the IPG 10 faster. This can be particularly beneficial when the external device 100 is used during a patient fitting session, but where the clinician only occasionally uses the external device 100 to transmit new payload data to the IPG 10. In this context, it is possible or likely that the clinician will want to send data to the IPG for a short time after a previous communication session has ended (FIG. 5, 220), and thus will want to reestablish communications quickly so that new payload data can be transmitted to the IPG 10 without undue delay. This is shown in FIG. 4A at time t6. Here, the external device 100 has determined that it has new payload data for the IPG 10 (FIG. 5, 220), and prepares this payload data and issues a listening window 132 (FIG. 5, 204). It is assumed in FIG. 4A that this listening window 132 issues while the IPG 10 is still in the fast advertising mode, because the fast advertising mode duration 112 has not yet been exceeded (FIG. 5, 218). Because the advertising data packets 130 issue more quickly in the fast advertisement mode, a packet will be received more quickly during the listening window 132. This allows the external device 100 to more quickly issue a connection request 134 (at time t7) (FIG. 5, 206), and the IPG 10 to issue an acknowledgement 135, which then starts a second communication session (Comm Session 2) (FIG. 5, 208). In short, the fast advertisement mode facilitates a quicker reconnection between the external device 100 and the IPG 10.

To save power in the IPG 10, it is preferred that the fast advertisement mode duration 112 is limited. Once this fast advertisement mode duration 112 has expired (FIG. 5, 218), it is preferred that the IPG 10 enter the slow advertisement mode (FIG. 5, 202). This example is shown in FIG. 4B. At time t8 (during Comm Session 2), data exchange between the external device 100 and IPG 10 has stopped, and at time t9 the inactivity duration 110 has been exceeded (FIG. 5, 212). As described earlier, this causes the IPG to send a disconnection instruction 138, which ends the communication session (Comm Session 2) (FIG. 5, 214). As just discussed, ending the communication session causes the IPG 10 to enter the fast advertisement mode (FIG. 5, 216) for duration 112 (FIG. 5, 218). In FIG. 4B, it is assumed that the fast advertising mode duration 112 has expired at time t10 before the external device 110 and IPG 10 can reconnect. Presumably, this is because the external device 100 does not presently have payload data prepared for the IPG.

To save power, the advertising algorithm 104 then enters the slow advertising mode at time t10 (FIG. 5, 202), which as noted earlier sends advertising data packets 130 less frequently (e.g., Adv Int 1=2.9 s). Thus, the external device 100 can still connect to the IPG 10, although this may occur more slowly. This is shown at time t11, when the external device 100 has once again prepared payload data for the IPG 10, and has issued a listening window 132 (FIG. 5, 204). Eventually an advertising data packet 130 is received 130 (although perhaps more slowly), and a connection request is sent at time t12 (FIG. 5, 206). The IPG 10 responds (ACK 135), and a new communication session (Comm Session 3) is started (FIG. 5, 208). In short, even though the fast advertisement mode is over, the external device can still connect with the IPG 10 in the slow advertising mode, which operates as the default advertising mode used to conserve power in the IPG 10.

Note that both the fast duration 112 and the inactivity period 110 can be adjusted to appropriate values based on user experience with the goal of reestablishing faster communications—i.e., with the goal of cause the external device 100 to connect with the IPG 10 during the fast advertising mode. For example, if the clinician realizes that he uses the external device 100 about every seven minutes or so, the inactivity period 110 and the fast advertisement mode duration 112 can be adjusted to improve the likelihood that the clinician will be able to re-establish communications quickly during the fast advertisement mode. For example, an inactivity duration of two minutes could be set in memory 110, while a fast advertisement mode duration of six minutes could be set in memory 112. Alternatively, an inactivity duration of five minutes could be set in memory 110, while a fast advertisement mode duration of three minutes could be set in memory 112. In either example, the sum of these durations (eight) is larger that the estimated seven-minute interval at which the clinician tends to use the external device 100, thus making it more likely that the external device 100 will quickly reconnect with the IPG 10 in the fast advertising mode.

In the example of the advertising algorithm 104 disclosed thus far, it has been assumed that advertising data packets are sent in slow and fast modes. However, this is not strictly necessary. For example, upon disconnecting from a communication session, the advertising algorithm 104 in the IPG 10 could send advertising data packets progressively more slowly. For example, the advertising data packets could be sent at a fast rate (e.g., every 0.3 second) for a first duration, then at a medium rate (e.g., every 1 sec) for a second duration, and then at a default slow rate (e.g., every 2.9 seconds). Still alternatively, the advertising interval could be gradually increased after disconnecting from a communication session.

It has also been assumed and illustrated thus far that the IPG 10 uses its advertising algorithm 104 to communicate with a single external device 100. For example, in FIG. 4A, the IPG 10 establishes a first communication session with external device 100 at time t3; eventually disconnects with the external device 100 at time t5; sends advertising data pursuant to the algorithm; and then later reconnects with this same external device 100 at time t7 for a second communication session. However, it is not strictly required that the IPG 10, through use of the advertising algorithm 104, will connect with only a single external device. For example, the IPG 10 can have a first communication session with a first external device 100 (t3); eventually disconnects with that external device 100 (t5); sends advertising data pursuant to the algorithm; and then later connects with a second external device 100' (t7) to which the IPG 10 has previously been paired.

Although disclosed in the context of an implantable medical device system that communicates in accordance with the Bluetooth or Bluetooth Low Energy communication standards, it should be appreciated that the invention is not limited to use of these communication standards.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. An implantable medical device (IMD) configured to communicate with an external device, comprising:
   control circuitry configured to:
      after terminating a first communication session, cause advertisement data to be repeatedly transmitted from the IMD to the external device, wherein the advertisement data is configured to allow a second communication session to be established between the IMD and the external device; and
      increase a time interval between the transmitted advertisement data over time.

2. The IMD of claim 1, wherein the control circuitry is programmed with an inactivity duration used to terminate the first communication session.

3. The IMD of claim 1, wherein the control circuitry is further configured to terminate the first communication session by transmitting a disconnection instruction.

4. The IMD of claim 1, wherein the control circuitry is configured to receive a connection request from the external device, and to transmit an acknowledgment to the external device in response to the connection request, to establish the second communication session.

5. The IMD of claim 1, wherein the control circuitry is configured to, after terminating the first communication session, cause the advertisement data to be repeatedly transmitted to the external device at a first time interval for a first duration, and thereafter to cause the advertisement data to be repeatedly transmitted to the external device at a second time interval, wherein the first time interval is shorter than the second time interval.

6. The IMD of claim 5, wherein the control circuitry is configured to store programmable values for the first duration, the first time interval, and the second time interval.

7. The IMD of claim 1, wherein the advertising data is transmitted using a Bluetooth or Bluetooth Low Energy communication standard.

8. The IMD of claim 1, wherein the control circuitry is further configured to establish the second communication session, wherein the second communications session enables the exchange of data between the IMD and the external device.

9. The IMD of claim 1, wherein the control circuitry is configured to terminate the first communication session with an external device that is different from the external device to which the advertisement data is repeatedly transmitted.

10. The IMD of claim 1, wherein the control circuitry is configured to terminate the first communication session with the external device.

11. A method for facilitating communications between an implantable medical device (IMD) and an external device, comprising:
- after terminating a first communication session, repeatedly transmitting from the IMD advertisement data to the external device, wherein the advertisement data is configured to allow a second communication session to be established between the IMD and the external device,
- wherein a time interval between the transmitted advertisement data increases over time.

12. The method of claim 11, wherein the first communication session is terminated using an inactivity duration stored in the IMD.

13. The method of claim 11, wherein the second communication session is established by receiving at the IMD a connection request from the external device, and by transmitting an acknowledgment from the IMD to the external device in response to the connection request.

14. The method of claim 11, wherein, after terminating the first communication session, the advertisement data is repeatedly transmitted to the external device at a first time interval for a first duration, and thereafter the advertisement data is repeatedly transmitted to the external device at a second time interval, wherein the first time interval is shorter than the second time interval.

15. The method of claim 14, further comprising programming into the IMD values for the first duration, the first time interval, and the second time interval.

16. The method of claim 11, wherein the advertising data is transmitted using a Bluetooth or Bluetooth Low Energy communication standard.

17. The method of claim 11, further comprising establishing the second communication session, wherein the second communications session enables the exchange of second data between the IMD and the external device.

18. The method of claim 11, wherein the first communication session is terminated with an external device that is different from the external device to which the advertisement data is repeatedly transmitted.

19. The method of claim 11, wherein the first communication session is terminated with the external device.

20. A non-transitory computer readable medium comprising instructions executable in an implantable medical device (IMD) to facilitate communications with an external device, wherein the instructions are configured when executed to cause the IMD to:
- after terminating a first communication session, repeatedly transmit from the IMD advertisement data to the external device, wherein the advertisement data is configured to allow a second communication session to be established between the IMD and the external device,
- wherein a time interval between the transmitted advertisement data increases over time.

* * * * *